United States Patent [19]

Burns

[11] Patent Number: 5,674,227
[45] Date of Patent: Oct. 7, 1997

[54] AFTERBIRTH RETAINING DEVICE

[76] Inventor: Margaret K. Burns, 172 Orchard La., Columbus, Ohio 43214

[21] Appl. No.: 647,399

[22] Filed: May 8, 1996

[51] Int. Cl.⁶ .................................................. A61B 17/42
[52] U.S. Cl. .................................................. 606/119
[58] Field of Search ...................... 606/1, 119–124; D24/274, 227; 206/564, 557, 370; 220/696, 719, 731, 752, 755; 433/77; 294/172

[56] References Cited

U.S. PATENT DOCUMENTS

| | | |
|---|---|---|
| 4,185,636 | 1/1980 | Gabbay et al. . |
| 4,477,112 | 10/1984 | Schülke ........................ 294/172 |
| 4,856,517 | 8/1989 | Collins et al. . |
| 5,002,561 | 3/1991 | Fisher . |
| 5,009,637 | 4/1991 | Cotey et al. . |
| 5,127,915 | 7/1992 | Mattson . |
| 5,415,651 | 5/1995 | Schmieding ........................ 606/1 |

*Primary Examiner*—Glenn Dawson
*Attorney, Agent, or Firm*—Thomas S. Baker, Jr.

[57] ABSTRACT

An afterbirth retaining device has a container for supporting a placenta and at least one clamp for securing an umbilical cord thereto. The container also has end walls, one of which has a handle and an adjacent handle shield. The retaining device is utilized by an individual to hold the afterbirth of a newborn child and safely permit the drawing of blood from the umbilical cord without accidentally sticking the individual with perhaps diseased or drug-containing blood.

7 Claims, 1 Drawing Sheet

AFTERBIRTH RETAINING DEVICE

FIELD OF THE INVENTION

This invention relates generally to an afterbirth retaining device and particularly concerns the safe withdrawal of a blood from an umbilical cord which is secured to clamps which are connected to a container of the retaining device. The container has a sidewall and a handle thereon so that the retaining device which is also capable of receiving a placenta, can be held in one hand and blood withdrawn from the umbilical cord by the other hand.

BACKGROUND OF THE INVENTION

It has become customary in hospitals to take blood samples from the umbilical cord of a newborn child to ascertain if the mother has ingested drugs, possibly leading to problems such as addiction in the child. Additionally, blood samples from the umbilical cord may be used to determine fetal acid and base status, and blood type of the fetus. The umbilical cord is typically wet, slimy, limp, and extremely difficult to handle and even more difficult to handle while attempting to insert a needle therein. Since numerous diseases are transported by human blood, hospital technicians do not want to be stuck by a needle while attempting to push the needle into the cord. With an ever increasing number of children born with drugs in the blood, the existence of HIV virus, and the like, many hospital technicians are reluctant to draw a blood sample.

I have provided an afterbirth device having a structure which provides for the generally safe withdrawal of blood from an umbilical cord.

SUMMARY OF THE INVENTION

To obtain the objectives of this invention, I have provided an afterbirth device generally having a container with at least one clamp. The container has a recess or base to hold the placenta and at least one end wall and desirably two. A handle is attached to one of the end walls which also has a splash guard or shield to prevent blood from contacting the holder of the device. The container, which generally can be rectangular, has at least one and desirably two generally upright extending clamps which are capable of holding and securing an umbilical cord in a taut position with little lateral movement. The clamps desirably have no moving parts and contain a securing member thereon such as teeth, serrations, etc., for securing the umbilical cord in a stationary position thus permitting the removal of blood therefrom with one hand of an individual while the remaining hand holds the retaining device.

Other advantages associated with the instant invention will become apparent from the drawings, detailed description, and claims, which follow.

DETAILED DESCRIPTION OF THE INVENTION

Figure 3:
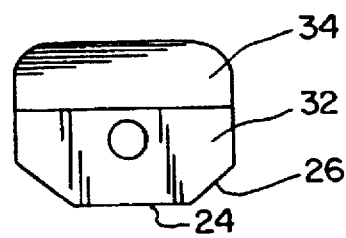
FIG. 3 is an end view of the device showing a handle and splash guard.

The afterbirth retaining device, generally indicated by the numeral 10, has a container assembly 20 and a plurality of clamps 50. The container comprises pan 22 which is generally rectangular and contains a central, longitudinal extending bottom recess or base 24. The base contains a plurality of grooves 30 which desirably extend in a longitudinal direction to keep a placenta 60 from moving in a lateral direction. In order to further retain the placenta within pan 22, the lateral outer portions 26 of the pan bottom are inclined outwardly in a generally vertical direction as best seen in FIG. 3. The lateral outer portions 26 also extend in a longitudinal direction and optionally may contain grooves, not shown, teeth, or other gripping elements to insure that the placenta is maintained within the pan portion of the container assembly 20. The height of the lateral outer portions 26 is not important so long as a majority, a substantial amount, or the entire placenta is contained generally below upper edge 29 thereof. Naturally, the longitudinal and lateral lengths of the pan are sufficient to contain an average size placenta therein.

Figure 1:
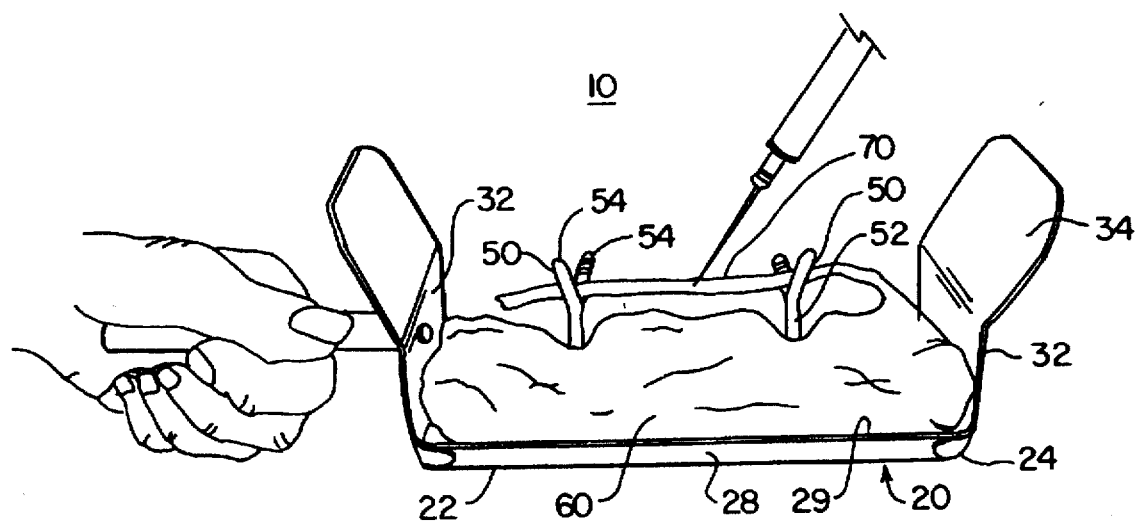
FIG. 1 is a perspective view of the afterbirth retaining device of the present invention showing the device being held by one hand which is shielded from a needle being inserted in an umbilical cord.
Figure 2:
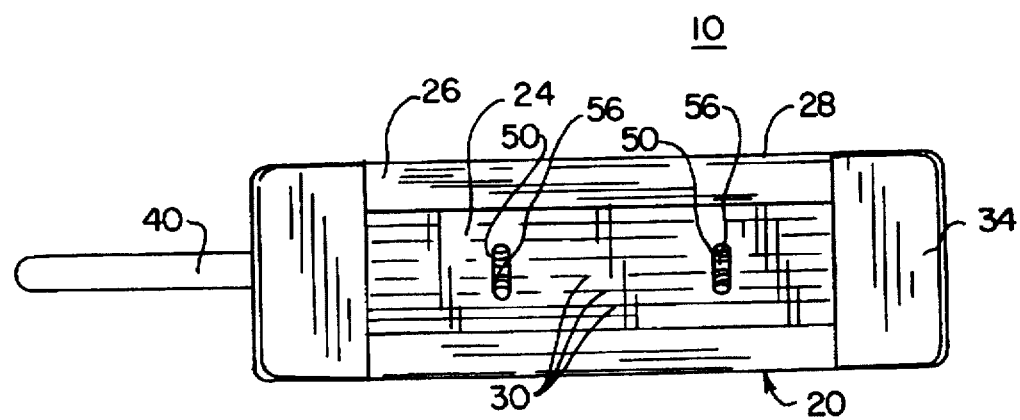
FIG. 2 is a top plan view of the retaining device of the present invention.

Container assembly 20 at the longitudinal boundary thereof contains at least one and preferably two end walls 32 as shown in FIG. 1. The end walls generally extend in a vertical direction to at least a distance above a normal-sized placenta and desirably a distance thereabove to readily retain the placenta when container assembly 20 is not held in a generally horizontal position. Adjacent to end wall 32 is a splash guard 34 which generally extends from the sidewall 32 upward and in a slightly longitudinally outward direction to form a shield. The purpose of the shield is to prevent blood from being sprayed or splashed upon the hand of an individual holding the afterbirth retaining device. The height of the shield is accordingly sized with this purpose in mind.

A handle 40 is secured to one of the end walls 32 in any conventional manner such as a bolt which extends through the end wall 32 and into the handle 40. The handle may be of any shape, size, or configuration such as simply a rod as shown in the drawings, or it can be a U-shaped device connected to the end wall at two points, or the like. Although the drawings only show one handle, a handle on each sidewall may be utilized for the sake of convenience.

At least one, but desirably two clamps, generally indicated by the number 50 are desirably connected to the center portion of base 24 in any suitable manner as by welding, through the use of fasteners, nuts and bolts, and the like. Clamps 50 are generally of any size or shape so long as they effect a secure engagement with umbilical cord 70 to generally keep it from sliding through the clamp upon a force exerted upon the cord. In other words, once the umbilical cord is secured to two clamps as in a taut manner, the cord generally maintains its position even upon a force exerted by a needle penetrating the cord. In a preferred embodiment and as shown in the drawings, clamp 50 has a generally upstanding leg 52 preferably extending in a vertical direction. The leg has a receptacle which may be two upstanding but diverging lateral arms 54 which extend from the upper portion of leg 52 to form a "Y" shaped clamp. The "Y" shaped clamp has a securing member 56 on the upper surface of the arms such as teeth, grooves, and the like to securely engage umbilical cord 70 and prevent it from moving in a longitudinal direction. Accordingly, the serrations, teeth, grooves, etc., desirably extend along the longitudinal length of the arms. In order that the umbilical cord can be readily secured to the arms, the height of the legs 52 is greater than the height of placenta 60 contained within pan 22.

The afterbirth retaining device 10 may be constructed of any suitable material such as plastic, metal, and the like with stainless steel being preferred.

The afterbirth retaining device 10 may be used in the following manner. Once a mother gives birth to a child, the afterbirth comprising a placenta 60 and an umbilical cord 70 attached thereto is placed in the base portion 24 of pan 22. The umbilical cord is strung through one of the clamps and pushed between the bottom portion of the upward but laterally diverging arms 52 so that teeth, etc., 56 may securely grasp the same. The remaining portion of the cord is drawn taut and applied to the remaining clamp and also forced to the bottom portion of the diverging arms 54 where it is also securely engaged by the securing member 56. Alternatively, the umbilical cord may be wrapped around an arm or arms of the first clamp and similarly wrapped around the arm or arms of the second clamp. An individual may then readily grasp the afterbirth retaining device by handle 40 and hold it in a suitable relationship with regard to the individuals's body so that with the remaining hand, a needle can be readily inserted into the umbilical cord and a blood sample taken. Since the cord is securely attached to the clamps 50 in a taut manner, there is little movement thereof. Moreover, the individual does not have to hold the umbilical cord which due to its wet, slippery and limp nature, can move and the individual accidentally prick or stab themselves with a blood-laden needle, perhaps containing drugs derived from the mother or Hepatitis, bacteria, or even HIV virus, etc. Pan 22 adequately retains the placenta and the individual's hand holding the retaining device is protected from any blood being splashed from injection of a needle into the umbilical cord by end wall 32 and splash guard While in accordance with the Patent Statutes, the best mode and preferred embodiment has been set forth, the scope of the invention is not limited thereto, but rather by the scope of the attached claims.

I claim my invention as follows:

1. An afterbirth retaining device for holding a placenta and an umbilical cord, comprising:

a container capable of receiving the placenta, said container having a first generally vertically extending end wall, a handle mounted on said first end wall, a splash shield affixed to said first end wall, and a second end wall on said container opposite said first end wall;

at least one umbilical cord clamp having an upstanding leg connected to said container and extending upwardly therefrom, a pair of diverging arms extending upwardly and laterally from said clamp leg;

a securing element on at least one of said arms for securing an umbilical cord thereto; and wherein said securing element comprises a plurality of grooves.

2. An afterbirth retaining device for holding a placenta and an umbilical cord, comprising:

a container assembly having a central pan for receiving a placenta defined by a base, a pair of lateral outer portions along two sides of said base and a pair of vertically upwardly extending end walls adjacent two sides of said base;

a handle affixed to one of said end walls and projecting laterally therefrom such that said end wall provides a shield between said handle and said central pan; and at least one umbilical cord clamp attached to said base.

3. The afterbirth retaining device of claim 2 further comprising a plurality of grooves formed in said base.

4. The afterbirth retaining device of claim 2 wherein said clamp has a leg and a pair of diverging arms at an outer end of said leg which arms extend upwardly and outwardly from said base.

5. The afterbirth retaining device of claim 4 further comprising a securing element on at least one of said arms.

6. The afterbirth retaining device of claim 5 wherein said securing element has a plurality of teeth.

7. The afterbirth retaining device of claim 4 further comprising a second umbilical cord clamp attached to said base.

* * * * *